United States Patent [19]

Bratton et al.

[11] Patent Number: 5,497,091
[45] Date of Patent: Mar. 5, 1996

[54] SURFACE MOUNTED PH SENSOR FOR CONE PENETRATION TESTING

[75] Inventors: Wesley L. Bratton, South Royalton; J. Christopher Bianchi, Pittsfield, both of Vt.

[73] Assignee: Applied Research Associates, Inc., Albuquerque, N.M.

[21] Appl. No.: 299,584

[22] Filed: Sep. 1, 1994

[51] Int. Cl.$^6$ .......................... G01N 33/22; G01N 33/24
[52] U.S. Cl. .......................... 324/348; 324/438; 324/449; 174/7; 204/288; 204/289
[58] Field of Search ..................... 324/348, 438, 324/448, 449, 452; 174/7; 204/288, 289

[56] References Cited

U.S. PATENT DOCUMENTS

| | | |
|---|---|---|
| 2,838,730 | 6/1958 | Lebourg . |
| 2,922,103 | 1/1960 | Smith . |
| 3,518,530 | 6/1970 | Wilson . |
| 4,350,051 | 9/1982 | Thompson ........................ 324/348 |
| 4,535,843 | 8/1985 | Jageler . |
| 4,575,410 | 3/1986 | Neti . |
| 5,110,441 | 5/1992 | Kinlen et al. . |
| 5,128,882 | 7/1992 | Cooper et al. . |
| 5,246,862 | 9/1993 | Grey et al. . |
| 5,387,869 | 2/1995 | Enomoto ........................... 324/348 |

OTHER PUBLICATIONS

Designation: D 3441–86, "Standard Test Method for Deep, Quasi–Static, Cone and Friction–Cone Penetration Tests of Soil[1]" pp. 469–474 (1986).

Primary Examiner—Kenneth A. Wieder
Assistant Examiner—Jose M. Solis
Attorney, Agent, or Firm—Jacobson, Price, Holman & Stern

[57] ABSTRACT

A surface-mounted pH sensor provides continuous pH profiling with depth during standard cone penetration testing (CPT). The pH sensor includes at least two electrodes, one being an antimony electrode and the other being a ceramic electrode. The electrodes are mounted to the shaft of a cone penetration device, and make contact with underground fluids during CPT. The antimony electrode, which functions as a measurement electrode, creates an exchange equilibrium between the hydrogen ions in the underground fluids and the ions of the antimony. This equilibrium creates a potential in the antimony electrode which is measured against the stable reference potential of the ceramic electrode. The resulting potential difference is indicative of the pH level of the underground fluids.

6 Claims, 3 Drawing Sheets

SURFACE MOUNTED PH SENSOR FOR CONE PENETRATION TESTING

FIELD OF THE INVENTION

The present invention provides for continuous, real time pH measurement as a pH sensor mounted on an exterior surface of a cone penetrometer probe is pushed into the ground during cone penetration testing (CPT).

BACKGROUND OF THE INVENTION

CPT test methods are governed by ASTM standard D-3441 "Standard Test Method for Deep, Quasi-Static, Cone and Friction-Cone Penetration Tests of Soil." CPT is a geotechnical technique for determining soil strength parameters of near surface soils to depths of approximately 300 ft. CPT uses hydraulically operated rams mounted on a specially designed truck to push various measurement probes into the soil. One meter long threaded, hollow steel pipe sections are used to incrementally lengthen the pushing stem. Electrical cables attached to the measurement probes are threaded through the hollow pipes and connected to electronic data acquisition and analysis equipment in the truck.

During the penetration process the forces required to advance the probe are recorded on the data acquisition system. This provides a continuous record of the soil parameters during the testing process.

Numerous instruments are used to detect groundwater contamination, such as turbidity, chemical concentration, fluorescence and pH. Typically, the pH measurements are performed by obtaining a sample from a monitoring well and conducting the test on the obtained sample in the laboratory.

Some applications of CPT and bore hole sampling are as follows:

U.S. Pat. No. 5,246,862 to Grey et al. discloses a penetrometer having a reagent carrying tape for detecting contaminants in soil while the penetrometer is driven into the ground. The tape is pressed against an optical window. Contaminants in the soil reacting with the reagent cause an optically sensible reaction in the tape to occur. Changes in the chemical character of the tape are determined and recorded.

U.S. Pat. No. 5,128,882 to Cooper et al. discloses a method and apparatus for real time, on-site detection and analysis of contaminant in soil. The apparatus continuously measures and records specific spectral properties of potentially contaminated soil along a typically vertical profile as a soil penetrating probe penetrates the soil. The probe is fitted with a light transparent window and a light source disposed internally of the probe. Light from internally of the probe passes through the window and is reflected back through the window from the soil as the probe passes through the soil. The light reflected from the soil back through the window is collected by a fiber optic link within the probe. The collected light is then transmitted through the fiber optic link to the surface for measurement and recordation of spectral distribution and intensity. The apparatus allows rapid on-site determination of location, depth, and quantity of contaminant in soils.

U.S. Pat. No. 4,535,843 to Jageler discloses an apparatus operable on a wireline logging cable for sampling and testing fluids in a bore hole and transmitting the results obtained from such testing to the surface. The apparatus includes a chamber having a three electrode system for measuring acidity (pH) and redox potential (Eh). At spaced intervals along the bore hole, a sample of fluid is drawn into the apparatus and tested. Conventional electrical circuits are used to send appropriate signals through a wireline to the surface where the ph and Eh of the formation fluid can be displayed or read out.

U.S. Pat. No. 3,518,530 to Wilson discloses a device for determining an electrochemical factor as the device is lowered into a hole. The electrochemical factor is recorded in relationship to another function, such as depth.

U.S. Pat. No. 2,922,103 to Smith discloses a device for measuring the electrical resistivity of well bore fluids while the device is being lowered through the well bore.

U.S. Pat. No. 2,838,730 to Lebourg discloses a device having electrodes for determining the resistivity of the mud in a bore hole.

SUMMARY OF THE INVENTION

By the present invention, a surface mounted pH sensor is used with CPT. Other CPT pH sensors do exist, but they require the operator to stop the CPT and draw a groundwater sample inside the probe where it is measured and then expelled. This procedure only allows discrete measurements to be made and not a continuous profile.

The present invention solves this problem and allows, for the first time, continuous profiling of groundwater pH readings with depth. Another unique aspect of the pH sensor of the present invention is that it is designed to survive the rugged environment experienced by the outside surface of the probe as it is pushed through all types of soil.

By the invention sensors are mounted on the exterior surface of the CPT in direct contact with the groundwater to be measured. No pre-drilled bore hole or open hole on a side of a probe is required. The sensors used are of a type disclosed in U.S. Pat. No. 5,110,441 to Kinlen et al. and U.S. Pat. No. 4,575,410 to Neti, hereby incorporated by reference.

U.S. Pat. No. 5,110,441 to Kinlen et al. discloses a solid state pH sensor having an indicator electrode of metal/metal oxide and a reference electrode of metal/metal salt applied to electrically conductive cermet conductors.

U.S. Pat. No. 4,575,410 to Neti discloses a solid state electrode system for measuring pH, including a pH electrode and a reference electrode. These electrodes are connected to a high input impedance potential measuring instrument which measures the voltage between the pH electrode and the reference electrode. This voltage is indicative of the hydrogen ion concentration in a test solution.

In the present invention, an exterior surface-mounted pH sensor provides continuous pH profiling with depth during standard cone penetration testing (CPT). The pH sensor includes at least two electrodes, one being an antimony electrode and the other being a reference electrode. The electrodes are mounted to the shaft of a cone penetration device, and continuously make contact with underground fluids during the CPT penetration.

The antimony electrode, which functions as a measurement electrode, creates an exchange equilibrium between the hydrogen ions in the underground fluids and the ions of the antimony. This equilibrium creates a potential on the antimony electrode which is measured against the stable reference potential of the reference electrode. The resulting potential difference (delta potential) is indicative of the pH level of the underground fluids.

Calibration of the penetrometer probe is accomplished by putting the probe assembly in pH buffered solution of known pH and watching the response. A three point calibration will be used initially but a periodic (after each penetration), one point check can later be performed. The response of the system is such that a continuous profile (site stratigraphy) of the pH over depth of penetration can be obtained during the cone penetration test.

Two types of electrodes may be used. In one embodiment, a ring electrode surrounds the penetrometer probe and is held in position by threaded sections of the probe. Alternatively, button electrodes may be threaded into threaded openings in the side of the probe. The inner end of the button electrodes is electrically interconnected with the other button electrodes to form an electrode with contact points on the outer surface of the probe.

Both of these types of electrodes include a measurement electrode of antimony material which create an exchange equilibrium with the hydrogen ions outside the probe and the ions on the antimony. This equilibrium is the source of the potential measured. The second electrode consists of a contact wire submerged in a reservoir of electrolyte filling solution and a liquid junction. In the present invention the liquid is a porous ceramic material. This electrode is the reference electrode and provides a stable reference potential against which the antimony electrode can be compared.

Accordingly, it is an object of the present invention to obtain a continuous pH measurement with depth of a penetrometer probe as a pH sensor located integral with and on the periphery of the probe is pushed into the ground with a cone penetrometer.

It is another object of the present invention to obtain a continuous pH measurement with depth of a penetrometer probe as a pH sensor located integral with and on the periphery of the probe is pushed into the ground with a cone penetrometer having at least two electrodes, one being an antimony electrode and the other being a reference electrode.

It is yet another object of the present invention to obtain a continuous pH measurement with depth of a penetrometer probe as a pH sensor located integral with and on the periphery of the probe is pushed into the ground with a cone penetrometer having at least two electrodes, one being an antimony electrode and the other being a reference electrode, with the electrodes being in an annular form or a button form.

These and other objects of the invention, as well as many of the intended advantages thereof, will become more readily apparent when reference is made to the following description taken in conjunction with the accompanying drawings.

DETAILED DESCRIPTION OF THE PREFERRED EMBODIMENTS

Figure 1:
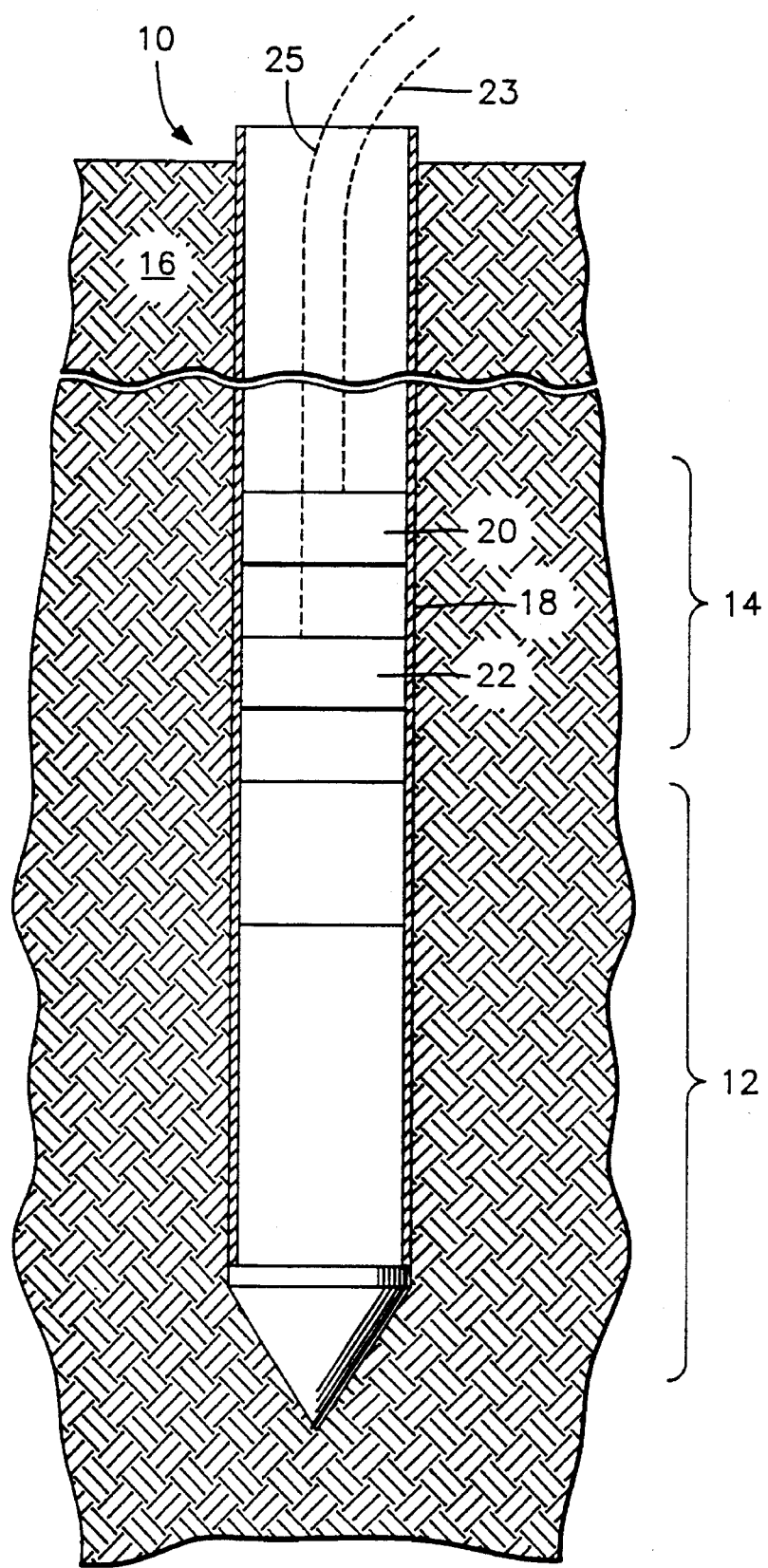
FIG. 1 is a sectional, schematic view of a pH CPT sensor being pushed into the ground with two ring-type electrodes located on a periphery of the penetrometer probe to allow simultaneous, continuous measurement of alkanity parameters from which soil contamination can be determined, and geotechnical parameters from which the soil stratigraphy is determined.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 2:
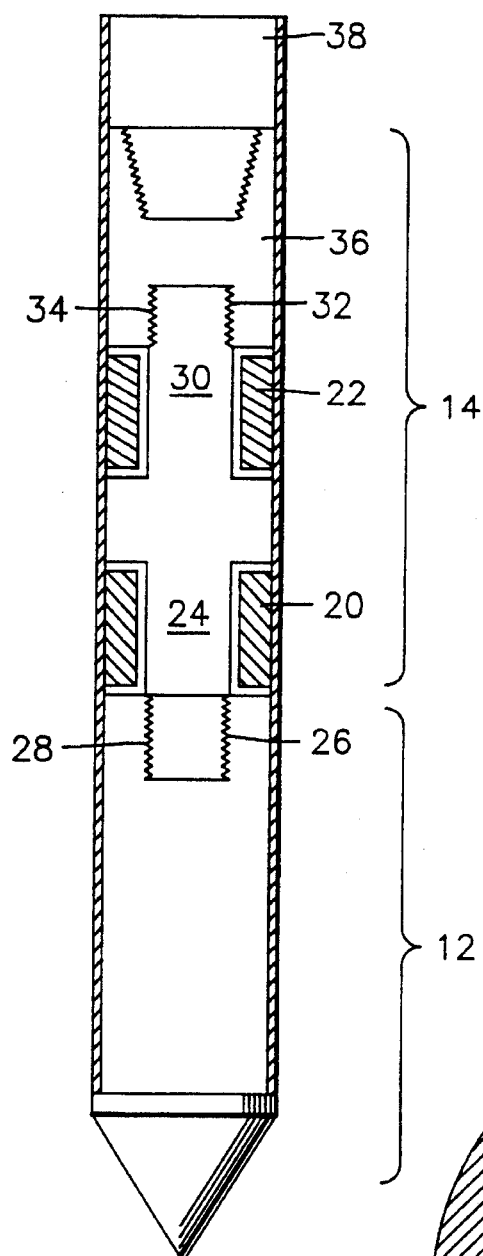
FIG. 2 is a sectional view of the cone penetrometer shown in FIG. 1.

With reference to the drawings, in general, and to FIGS. 1 and 2, in particular, a cone penetrometer embodying the teachings of the subject invention is generally designated as 10. With reference to its orientation in FIG. 1, the cone penetrometer includes an ASTM cone section 12 and a pH probe section 14. In accordance with the invention, the cone penetrometer 10 is pushed through soil 16 according to the known method as disclosed in U.S. Pat. Nos. 5,128,882 and 5,246,862 herein incorporated by reference and ASTM designation D3441-86.

Mounted on a peripheral exterior surface 18 of the probe 14 are two annular electrodes 20, 22. Electrode 20 is a ceramic reference electrode connected by an electric cable 23 to a location above ground for analysis of the pH values of the groundwater in the earth through which the cone penetrometer is pushed. Similarly, antimony electrode 22 includes an electric cable 25 passing through the penetrometer rods to the surface for continuous pH measurements.

By the present invention, continuous measurements are made below the ground surface by installation of a pH sensor formed by two electrodes made of antimony and a ceramic material, respectively, located on a peripheral exterior surface of a penetrometer probe. The outer peripheral surface of the annular elements is continuous with a peripheral outer surface of the probe for continuous contact with the earth as the probe passes through the earth during cone penetration testing.

The penetrometer probe, along with the two electrodes, are pushed into the ground using the hydraulic force of a cone penetrator. The two electrodes forming the pH sensor of the present invention are in direct contact with the soil to provide continuous measurements to the surface through electric cables inside penetrometer rods. The penetrometer probe 12 allows simultaneous measurement of geotechnical parameters from which the soil stratigraphy can be determined.

With reference to FIG. 2, annular electrode 22 is located surrounding a recessed portion 24 of pH probe section 14. Threads 26 on the exterior surface of section 24 engage with internal threads 28 of cone section 12 for securing annular electrode 20 between the probe 14 and the cone 12. Similarly, annular electrode 20 is placed around recessed section 30 with external threads 32 engaged with internal threads 34 of penetrometer rod connector 36. Probe section 14 and rods 38 are hollow for passage of electric cables 23 and 25 to the surface.

Figure 4:
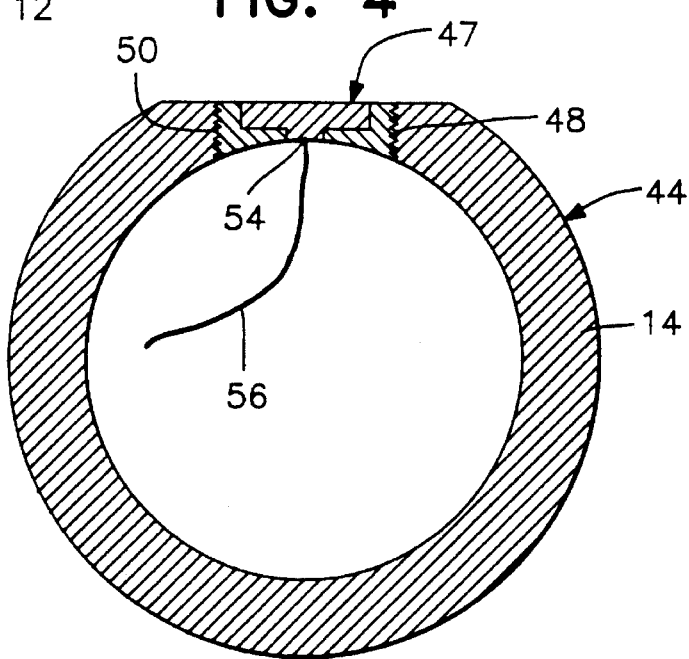
FIG. 4 is an enlarged cross-sectional view taken through one of the electrodes in FIG. 3.

In an alternative embodiment, the antimony and reference electrodes are formed by two circular buttons 40 and 58 which, with reference to FIG. 4, have an exterior surface 42 continuous with a peripheral exterior surface 44 of probe 14 for contact with soil during depth penetration. External threads 48 engage with internal threads 50 of the probe section 14.

An innermost surface of the button 40 includes an electrical contact point 54 to which is connected an electrical cable 56. Electrical cable 56 is electrically connected to a cable passing through the cone penetrometer to the surface for obtaining continuous pH measurements during penetration of the cone penetrometer into the earth.

Figure 3:
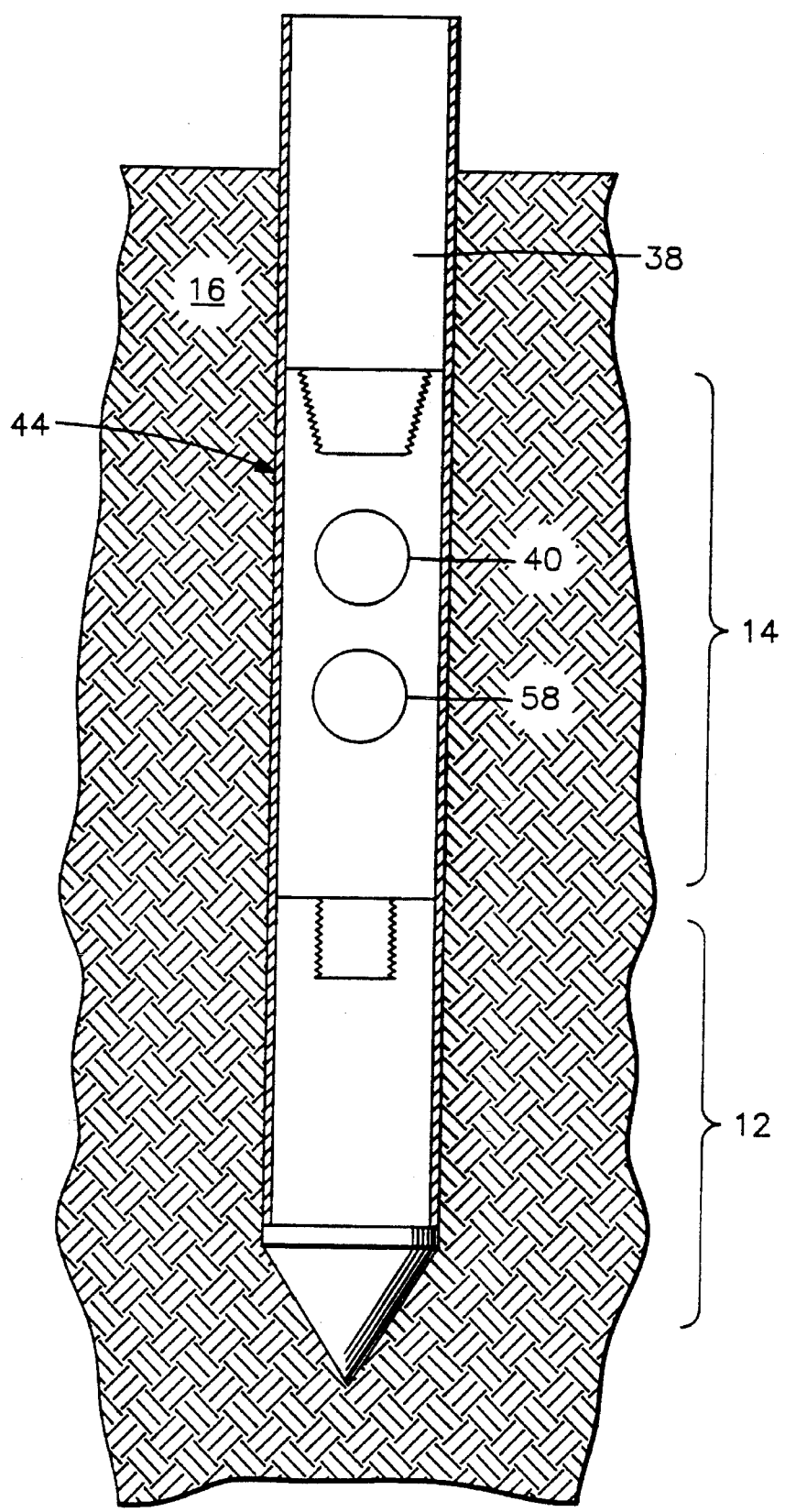
FIG. 3 illustrates a cone penetrometer with alternative type of electrodes located on the periphery of the penetrometer probe.

The cone penetrometer shown in FIG. 3 also includes a one button ceramic reference electrode 58 which is connected in a manner similar to the connection for the antimony button electrode shown in FIG. 4. A cable passing through the cone penetrometer to the surface of the soil provides an electrical connection to obtain continuous pH value measurements during cone penetration testing.

Having described the invention, many modifications thereto will become apparent to those skilled in the art to which it pertains without deviation from the spirit of the invention as defined by the scope of the appended claims.

We claim:

1. An apparatus for providing continuous pH measurements of soil in real time during soil penetration, said apparatus comprising:

a cone penetrometer test apparatus including a penetrometer probe for penetrating the soil to a depth of up to 300 feet, at least two electrodes mounted on a peripheral exterior surface of said penetrometer probe, one of said electrodes being a reference electrode and another one of said electrodes being a measurement electrode made of antimony, and means for transmitting a continuous electrical potential difference during depth penetration of said penetrometer probe through the soil from said at least two electrodes to a surface of the soil for continuous, real time measurement of pH simultaneously with continuous penetration of the soil by the penetrometer probe.

2. An apparatus according to claim 1, wherein a radially outermost surface of said at least two electrodes is continuous with said peripheral exterior surface of said penetrometer probe.

3. An apparatus according to claim 2, wherein said at least two electrodes are annular rings.

4. An apparatus according to claim 2, wherein said at least two electrodes are button-shaped.

5. An apparatus according to claim 4, wherein said buttons of one electrode are electrically interconnected.

6. An apparatus according to claim 1, wherein said reference electrode is made of ceramic material.

* * * * *